United States Patent [19]

Boucher et al.

[11] Patent Number: 4,810,090

[45] Date of Patent: Mar. 7, 1989

[54] METHOD AND APPARATUS FOR MONITORING BLOOD COMPONENTS

[75] Inventors: Terry D. Boucher, Littleton; Brian M. Holmes, Golden, both of Colo.

[73] Assignee: Cobe Laboratories, Inc., Lakewood, Colo.

[21] Appl. No.: 88,686

[22] Filed: Aug. 24, 1987

[51] Int. Cl.⁴ .................. G01N 33/49; G01N 21/05
[52] U.S. Cl. ........................ 356/39; 356/73; 356/410; 250/576
[58] Field of Search ............ 356/39, 40, 41, 73, 356/244, 410, 440; 250/576

[56] References Cited

U.S. PATENT DOCUMENTS

| | | | |
|---|---|---|---|
| 2,835,252 | 5/1958 | Mauchel | 356/39 |
| 3,666,941 | 5/1970 | Watson | 356/246 |
| 3,785,735 | 1/1974 | Friedman et al. | 356/39 |
| 4,132,349 | 1/1979 | Khoja et al. | 74/722 |
| 4,201,471 | 5/1980 | Pitt et al. | 356/73 X |
| 4,229,179 | 10/1980 | Lee | 356/246 X |
| 4,305,659 | 12/1981 | Bilstad et al. | 356/40 |
| 4,326,806 | 4/1982 | Donner | 356/440 X |
| 4,350,441 | 9/1982 | Wicnienski | 356/40 |
| 4,522,494 | 6/1985 | Bonner | 356/39 |
| 4,577,964 | 3/1986 | Hanson, Jr. | 356/39 |
| 4,657,383 | 4/1987 | Bellhouse | 356/39 |

FOREIGN PATENT DOCUMENTS 8101467  5/1981  World Int. Prop. O. ......... 356/410

OTHER PUBLICATIONS

Cobe 2997 Operator's Manual, Title, pp. 2-7 to 2-8, 1985.
Fenwel CS-3000 Operator's Manual, Title, pp. 4-9, 4-12, 5-12, 5-13, 1983.

Primary Examiner—Vincent P. McGraw

[57] ABSTRACT

Monitoring concentration of components of blood flowing through a flowpath including flowing the components through a transparent channel, directing light to the channel along an axis intersecting the channel, detecting light passing through the channel along the axis, detecting light scattered off of the axis, and determining concentration of components based on the light passing along the axis and/or the light scattered off of the axis. Also disclosed is a movable cover to block ambient light from a photodetector after mounting of a removable transparent flow channel.

27 Claims, 1 Drawing Sheet

METHOD AND APPARATUS FOR MONITORING BLOOD COMPONENTS

FIELD OF THE INVENTION

This invention relates to monitoring components of blood flowing in a flowpath, e.g., platelets flowing through an outflow line of a continuous blood separator.

BACKGROUND OF THE INVENTION

In continuous blood seprators, whole blood is separated into various fractions, e.g., red blood cells, plasma, and platelets. In such apparatus, it is desirable to know if there is spillover on one type of component (e.g., red cells) into an outflow line for a different component (e.g., platelets).

In a platelet collection procedure, the platelets are collected in a bag, and the red blood cells and plasma are returned to the patient. The bags of platelets can be stored, for example, up to five days, before use. Bellhouse U.S. Pat. No. 4,657,383 and Bonner U.S. Pat. No. 4,522,494 disclose analyzing volumes of collected platelets stored in bags for platelet viability by sensing the light passed through samples that are still in the bags and are caused to flow back and forth, one measurement parameter being concentration of platelets in the bags.

Khoja et al. U.S. Pat. No. 4,132,349 discloses monitoring the optical density of light passing through a white blood cell outflow line and using the optical density to control outflow pump motors.

SUMMARY OF THE INVENTION

In one aspect the invention features monitoring the condition of components of blood flowing through a transparent channel by directing light along an axis through the channel, detecting light passing through the channel along the axis with a central detector, detecting light scattered off of the axis with an annular detector, and determining the concentration of components based upon both the transmitted light and scattered light measurements (e.g., a ratio of the two) or upon either measurement alone, using a measurement providing desired accuracy depending upon sample conditions.

In preferred embodiments the light detected by the central detector is used to measure concentration in a low concentration range, and the light detected by the annular detector is used to measure concentration in a high range, thereby permitting detection of concentration over a larger range of concentration than either measurement along would permit; the central detector is used to determine concentrations below a point of inflection of the irradiance versus concentration function for the light detected by the annular detector, and the annular detector is used for concentrations above two times the inflection point concentration; two different light sources having different sensitivities in different ranges are used to increase the range; a photodetector is used to sense the light, and normalized irradiance values are employed; and the channel is part of a flow line of a disposable tubing set of a blood centrifuge.

In another aspect the invention features using a removable transparent channel with a permanent light source and photodetector mounted so as to provide a space for receiving the channel and a movable cover for fitting tightly over the channel to block out ambient light.

In preferred embodiments the cover is slidably mounted along an axis parallel to an axis through the light source and photodetector; the cover includes notches for receiving portions of the channel to accurately locate the channel; the cover is spring biased toward the closed position; the channel has flat walls normal to the direction of travel of the light; the flow area through the channel is approximately equal to that through the tubes leading to it, and there is smooth transition between the two.

Other features and advantages of the invention will be apparent from the following description of a preferred embodiment thereof and from the claims.

DRAWINGS

DESCRIPTION OF THE PREFERRED EMBODIMENT

The preferred embodiment will now be described.

Structure

Figure 1:
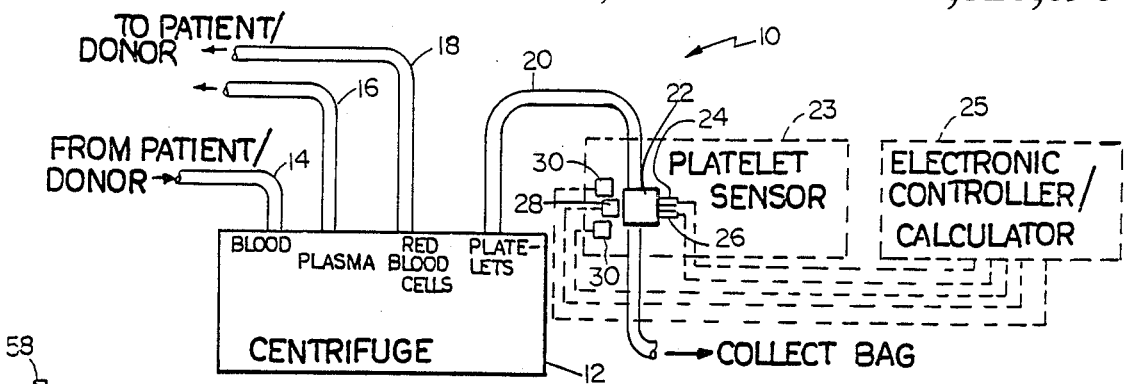
FIG. 1 is a block diagram of a centrifugal blood separating system according to the invention.

Referring to FIG. 1, there is shown centrifugal blood separating system 10 including centrifuge 12, which is shown diagrammatically and includes a disposable plastic separation channel of the general type disclosed in Kellogg et al. U.S. Pat. No. 4,094,461 in a rotating bowl (all not shown). Centrifuge 12 is connected to blood inflow line 14, plasma outflow line 16, red blood cell outflow line 18, and platelet outflow line 20, which includes on it optically-transparent polycarbonate cuvette 22. Cuvette 22 is adapted to be received in platelet sensor 23, which includes red light-emitting diode (LED) 24, green LED 26, central photodetector 28, and annular photodetectors 30. LED's 24, 26 and photodetectors 28, 30 are electrically connected to electronic controller/calculator 25. Flow lines 14, 16, 18, and 20 and the separation channel (not shown) of centrifuge 12 are part of a disposable plastic tubing set that includes other components and is used with a particular patient/donor during a blood separation procedure. The disposable tubing set is mounted on a blood separation monitor that includes the rotating bowl (not shown) of centrifuge 12, platelet sensor 23, electronic controller/calculator 25 and various pumps, pinch valves, and other sensors for interacting with the disposable tubing set (not shown).

Figure 2:
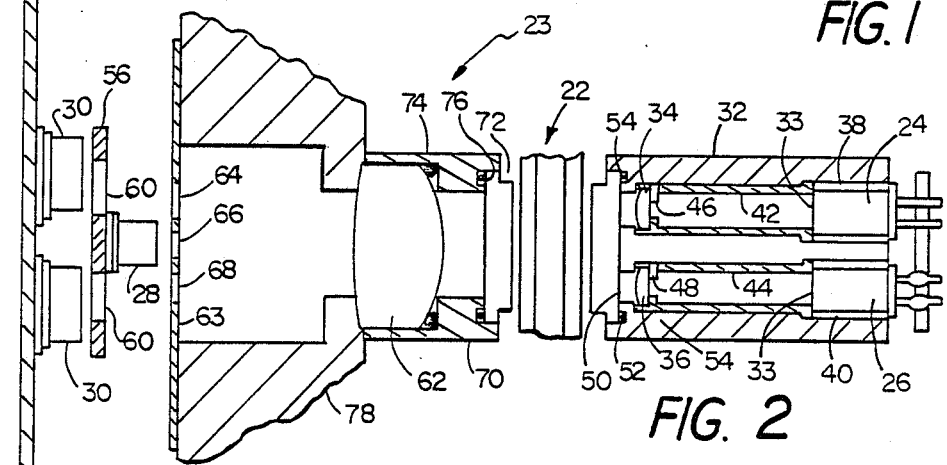
FIG. 2 is a diagrammatic partially sectional view of optical measuring components of the FIG. 1 apparatus.
Figure 3:
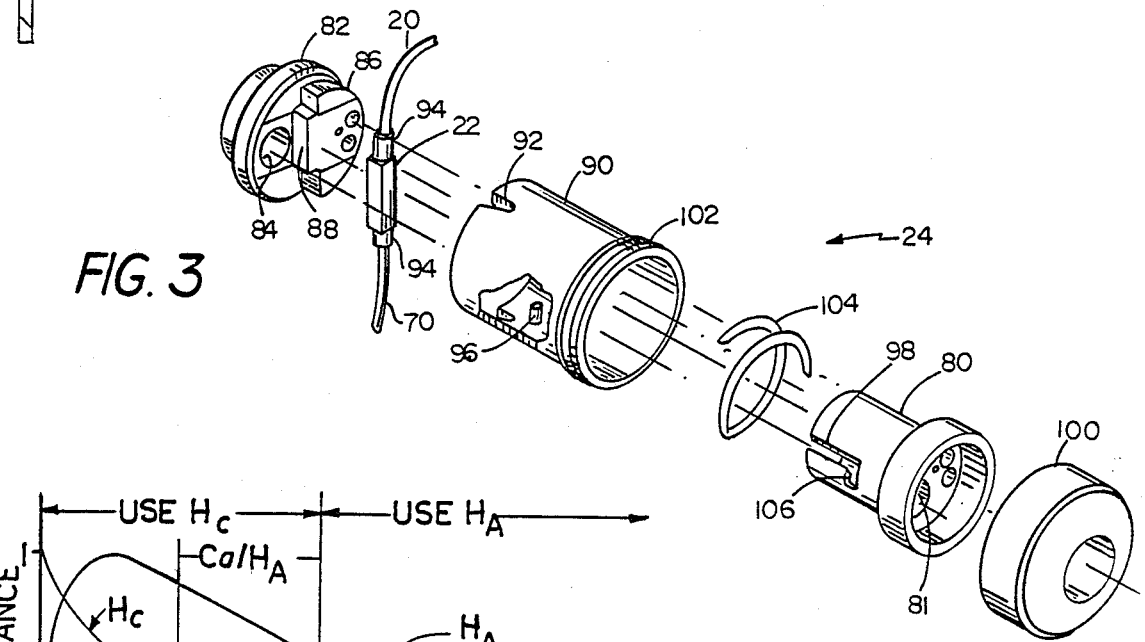
FIG. 3 is a diagrammatic perspective view of components used for mounting and covering the FIG. 2 components.

Referring to FIGS. 2 and 3, the components of platelet sensor 23 that are used with cuvette 22 to sense the platelet concentration therein are shown. The optical components are shown in FIG. 2, and associated mounting and removable cover components are shown in FIG. 3. Referring to FIG. 2, red and green LED's 24, 26 are mounted within sleeve 32 behind 0.053" pin hole shims 33 and are maintained in proper position with respect to their respective focusing lenses 34, 36 via bushings 38, 40 and flanged bushings 42, 44. A 0.04"

orifice stop 46 is provided at lens 34, and a 0.110" orifice stop 48 is provided at lens 36, in order to provide more green light from LED 26. Window 50, through which the light from LED's 24, 26 is directed, is sealed to sleeve 32 via O-ring 52, and O-rings 54 provide seals between lenses 34, 36 and sleeve 32, to prevent dust or other particles from getting between window 50 and lenses 34, 36. On the other side of cuvette 22, central photodetector 28 is mounted on circuit board 56, and annular photodetectors 30 are mounted on circuit board 58 behind circuit board 56. Annular photodetectors 30 are aligned with holes 60 in circuit board 56 to permit light focused by lens 62 to be received at photodetectors 30. Baffle 63, between the photodetectors and lens 62, similarly has three holes 64, 66, 68 for permitting light focused by lens 62 to be directed to annular photodetector 30 via holes 64, 68 and to central photodetector 28 via hole 66. Lens 62 is mounted in sleeve 70, on which is also mounted window 72. An O-ring seal is provided between lens 62, window 72 and sleeve 70 via O-rings 74, 76. Lens 62 is spaced from baffle 63 via housing 78, only a small portion of which is shown.

Referring to FIG. 3, window retainer 82 includes cylindrical bore 84 for receiving sleeve 70 and lens 62 therein. Retainer 82 is mounted on the face of the centrifuge control monitor, and the remaining components behind sleeve 70 shown in FIG. 2 are behind sleeve 70 and within the control monitor. Middle housing 86 is fixedly mounted on the face of window retainer 82, and upper housing 80 is fixedly mounted on middle housing 86, extending outward from the face of the control panel. Upper housing 80 includes cylindrical bore 81 for receiving sleeve 32 and LED's 24, 26 therein. Upper housing 80 defines with window retainer 82 and vertical surface 88 of middle housing 86 a region for receiving and aligning rectangular cuvette 22.

Vertical surface 88 properly aligns cuvette 22 in the path of travel of light from LED's 24, 26 to lens 62. Cover 90 is slidably mounted on upper housing 80 and has converging notches 92 for receiving cylindrical extensions 94 of cuvette 22 and an inwardly directed projection 96 received in slot 98 of outer housing 80. In FIG. 3 slot 98 is shown in a position rotated approximately 150° from its true position in which it is aligned with projection 96. Cap 100 is threadedly secured to threads 102 of cover 90. Compression spring 104 is received within cover 90 and acts to bias cover 90 toward window retainer 82 to place it in a closed position during operation. Cover 90 can thus be slided axially outward with respect to upper housing 80 with projection 96 sliding in slot 98, and cover 90 can be temporarily locked in the outward position by rotating it counterclockwise, so that projection 96 is received in small transverse extension 106 of slot 98.

Cuvette 22 has approximately a 3 mm inner dimension, and tube 20 has a 0.113" inner diameter. At the junction between the circular flowpath of tube 20 and the rectangular flowpath of cuvette 22, there is a smooth transition to avoid turbulence and promote laminar flow. The cross-sectional flow areas of tube 20 and cuvette 22 are similar for the same purpose. Cuvette 22 is made of optically clear polycarbonate selected for its ease of molding characteristics. The outer and inner surfaces of the walls of cuvette 22 are made as flat as possible in order to limit refraction.

Annular detectors 30 are positioned to receive forward small angle scatter having angles between 6° and 14°. Holes 64, 66, 68 act as stops for light, preventing reflected light that is not within the proper scatter angle from passing back to the photodetectors. The light received at central photodetector 28 has a central target radius angle, $\theta_1$, of $\pm 5°$. The outside annular radius, $\theta_2$, is 14°, and the inside annular radius, $\theta_2$, is 6°. The particle diameter, a, for platelets is approximately 3 microns. Lenses 34, 36 focus the light from their respective LED's on central detector 28; lens 62 permits light from both sources to be directed to central detector 28.

Operation

In use with a new patient/donor, the disposable tube set including tubes 14, 16, 18, 20, and the channel of centrifuge 12 is mounted on the blood centrifuge monitor, including mounting of cuvette 22 in platelet sensor 23. Prior to mounting, cover 90 is moved from a closed position, in which it is biased by spring 104 against the periphery of window retainer 82, to an open position by sliding cover 90 outward, projection 96 sliding in slot 98 until it hits the end of the axial portion of slot 98, and then rotating cover 90 counterclockwise so that projection 96 sits within the transverse extension 106. In this open position, the bottom of cover 90 is spaced from window retainer 82, and cuvette 22 can be mounted in position against vertical wall 88. Cover 90 is then released, and it slides back into position with converging slots 92 engaging circular extensions 94 of cuvette 22 and properly aligning and holding cuvette 22 in place. With the exception of a small leakage associated with slots 92, cuvette 22 is protected from ambient light by cover 90.

The centrifuge apparatus is then primed with saline solution prior to connection to a patient/donor. Cuvette 22 is subjected to positive pressure prior to pumping saline into cuvette 22 in order to minimize microbubbles in the cuvette optical regions.

In making measurements, LED's 24, 26 are turned on at separate times and are pulsed on and off during their turns to read zero offset voltages. The red light is infrared, peaked at a wavelength of 875 nm, and the green light is peaked at a wavelength of 565 nm. The resolution of light detection is 0.1%, owing to use of a 10-bit analog to digital (A/D) conversion of the analog voltages provided by photodetectors 28, 30. There is a delay from the time that the LED is turned on to the A/D reading of at least 20 microseconds. Sixteen samples, one per pulse, are used and averaged for each voltage reading, and they are taken at frequency of 953 hz, which is close to an even multiple of the 120 hz predominant ambient light to reduce noise. The two annular photodetector voltages are similarly averaged together.

After saline has been in cuvette 22 for at least one minute, electronic controller/calculator 25 automaically adjusts the two LED pulsed currents to values that result in full-scale green-central photodetector voltage, $V_{GC}$, and full-scale red-central photodetector voltage, $V_{RC}$, within 3% of each other. The LED currents are then held constant to enable electronic controller 25 to read and store the following voltages:

$V_{GCS}$ = green-central irradiance-saline voltage
$V_{RCS}$ = red-central irradiance-saline voltage
$V_{GAS}$ = green-annular irradiance-saline voltage
$V_{RAS}$ = red-annular irradiance-saline voltage During a platelet collection blood separation procedure, centrifuge 10 receives whole blood through line 14 and separates it into plasma, red blood cell, and platelet fractions, which leave centrifuge 12 via their respective outflow lines 16, 18, 20. As described in more detail below, the platelet concentration in line 20 is monitored during the separation procedure by platelet sensor 23, and used by controller/calculator 25 to display the concentration in the collect bag and to update a prerun platelet yield calculation. Platelet sensor 23 is also used to detect spillovers of red blood cells into platelet outflow line 20. The concentration and spillover condition is based upon irradiance values, H, based upon voltages of photodetectors 28, 30. The voltages measured by central and annular detectors 28, 30 during the times when the green and red lights are pulsed on are as follows:

$V_{GC}$ = green central voltage
$V_{RC}$ = red central voltage
$V_{GA}$ = green annular voltage
$V_{RA}$ = red annular voltage During the LED off cycles, the following offset voltages are measured:

$V_{GCO}$ = green-central irradiance offset voltage (LED off)
$V_{RCO}$ = red-central irradiance offset voltage (LED off)
$V_{GAO}$ = green annular irradiance offset voltage (LED off)
$V_{RAO}$ = red annular irradiance offset voltage (LED off)

Based upon these measured voltages, the following normalized irradiance values are obtained for use in determining platelet concentration and generation of ratios:

$$H_{GC} = \frac{V_{GC} - V_{GCO}}{V_{GCS} - V_{GCO}} \quad \text{green central irradiance ratio}$$

$$H_{RC} = \frac{V_{RC} - V_{RCO}}{V_{RCS} - V_{RCO}} \quad \text{red central irradiance ratio}$$

$$H_{GA} = V_{GA} - V_{GAO} \quad \text{green annular irradiance}$$

$$H_{RA} = V_{RA} - V_{RAO} \quad \text{red annular irradiance}$$

The central irradiance, $H_C$, can be related to the platelet concentration N by the following equation:

$$H_C = 1 - (1 - e^{-C_2 Nl}) e^{\left(\frac{-C_1 \theta_1^2 a^2}{C_2 Nl + C_3 a^2}\right)} \quad (1)$$

where:
N = concentration $\times 10^6$/microliter
l = sample thickness in millimeters (i.e., 3 mm)
$\theta_1$ = central target radius angle in degrees (i.e., 10°)
a = particle diameter in microns (i.e., 3 u)

The annular irradiance, $H_A$, can be related to platelet concentration, N, by the following equation.

$$H_A = C_4 (1 - e^{-C_2 Nl}) \left( e^{-\frac{C_1 \theta_3^2 a}{C_2 Nl + C_3 a^2}} - e^{-\frac{C_1 \theta_2^2 a^2}{C_2 Nl + C_3 a^2}} \right) \quad (2)$$

where:
$\theta_3$ = outside annular radius in degrees (i.e., 14°)
$\theta_2$ = inside annular radius in degrees (i.e., 6°)

Figure 4:
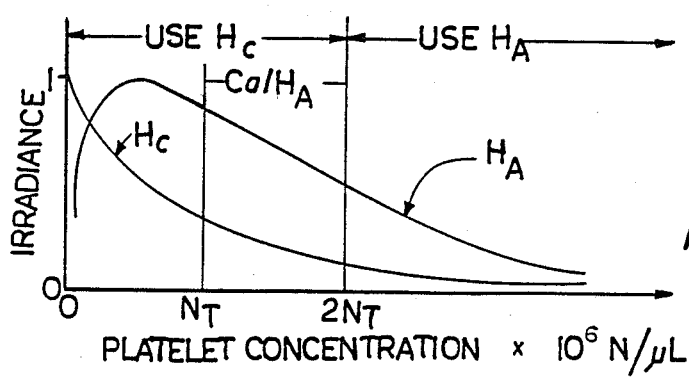
FIG. 4 is a graph of irradiance versus platelet concentration for a central detector and an annular detector of the FIG. 1 apparatus.

Equations 1 and 2 have the forms shown in FIG. 4. $N_T$ is the platelet concentration at which the curve for $H_A$ has a point of inflection; i.e., the rate of change of the slope crosses 0. In determining platelet concentration, the central detector irradiance values, $H_C$, are used for concentrations between 0 and $N_T$, because within this range, there are significant changes in irradiance with changes in concentration. This would not be a good range for the annular detector curve, as there is a peak within this range, and thus some annular irradiance values correspond to two different concentration values. The annular detector curve is used for concentrations above $2N_T$, as there are still significant changes in annular irradiance with changes in concentration, while there are only very small changes in central irradiance with further increases in concentration. Between the $N_T$ and $2N_T$ concentrations, either the annular or the central irradiance values provide good measure of concentration.

Because equations 1 and 2 cannot be directly solved for N based upon measured $H_{GC}$, $H_{RC}$, $H_{GA}$, and $H_{RA}$ values, and because these equations do not easily converge to a solution using an iterative procedure, the irradiance curves are empirically fit to a sum of exponentials in order to simplify the iterative solution convergence. The equations employed are as follows:

$$H_{CG} = C_{1G} e^{-\alpha_{1G} N} + C_{2G} e^{-\alpha_{2G} N} + C_{3G} e^{-\alpha_{3G} N} \quad (3)$$

where: constants $C_{1G} + C_{2G} + C_{3G} = 1$ and constants $\alpha_{IR} > \alpha_{2R} > \alpha_{3R}$ $$H_{CR} = C_{1R} e^{-\alpha_{1R} N} + C_{2R} e^{-\alpha_{2R} N} + C_{3R} e^{-\alpha_{3R} N} \quad (4)$$

where: constants $C_{1R} + C_{2R} + C_{3R} = 1$ and $\alpha_{IR} > \alpha_{2R} > \alpha_{3R}$ $$ag H_{GA} = A_{1G} e^{-\beta_{1G}(N - N_T)} + A_{2G} e^{-\beta_{2G}(N - N_T)} + A_{3G} e^{-\beta_{3G}(N - N_T)} \quad (5)$$

where: $\beta_{1G} > \beta_{2G} > \beta_{3G}$ $$ar H_{RA} = A_{1R} e^{-\beta_{1R}(N - N_T)} + A_{2R} e^{-\beta_{2R}(N - N_T)} + A_{3R} e^{-\beta_{3R}(N - N_T)} \quad (6)$$

where: $\beta_{1R} > \beta_{2R} > \beta_{3R}$

The C, $\alpha$, ag, ar, A, $\beta$, and $N_T$ constants for a particular optical system are determined, prior to use of the apparatus with patients/donors, by regression analysis to provide a best fit for measured irradiance values for samples of known platelet concentration. The ag and ar scale factors may have to be adjusted during use with each patient/donor by determining N using the $H_C$ curve when in the $N_T$ to $2N_T$ range, and plugging this value of N in the $H_A$ curve. To obtain platelet concentration, N, during operation, equations 3 and 4 are rearranged in the following form:

$$\underset{LHS}{H_c e^{\alpha_1 N}} = \underset{RHS}{C_1 + C_2 e^{(\alpha_1 - \alpha_2)N} + C_3 e^{(\alpha_1 - \alpha_3)N}} \quad (7)$$

The left-hand side (LHS) and the right-hand side (RHS) of Equation 7 are then separately calculated for values of N until the LHS equals the RHS; when this condition has been achieved, the value of N is the one that corresponds to the irradiance value $H_C$. In the iterative procedure, an arbitrary starting value of $N_n$ ($N_0$), is selected and plugged into the RHS of Equation 7. The next value for N, $N_{n+1}$, is obtained by inserting it into the LHS and equating this to the RHS value just calculated for $N = N_n$, as given by Equation 8 below.

$$N_{n+1} = \frac{1}{\alpha_1} \ln\left[\frac{RHS \text{ with } N = N_n}{H_C}\right] \quad (8)$$

The convergence is then checked by comparing the difference in the values of $N_{n+1}$ and $N_n$. When these values are within ±1%, the iterative procedure is stopped. If the difference is greater than 1%, the steps are repeated (e.g., plugging the $N_{n+1}$ value into RHS and inserting $N_{n+2}$ into LHS and solving for $N_{n+2}$) until they do.

A similar procedure is used to iteratively solve Equations 5 and 6 for N, using rearranged equivalent Equation 10 below:

$$\underbrace{aH_A e^{\beta_1(N-N_T)}}_{LHS} = \underbrace{A_1 + A_2 e^{(\beta_1-\beta_2)(N-N_T)} + A_3 e^{(\beta_1-\beta_3)(N-N_T)}}_{RHS} \quad (10)$$

An arbitrary value of N is selected and plugged into the right-hand side. A new value for N, $N_{n+1}$, is given by Equation 11 below:

$$N_{n+1} = N_T + \frac{1}{\beta_1} \ln\left[\frac{RHS \text{ with } N = N_n}{aH_A}\right] \quad (11)$$

Convergence is checked, and these steps are repeated until the difference between successive N values is within ±1%.

By using both an annular detector and a central detector, the range of concentration that can measured is expanded over the range provided by a single detector. Also, the irradiance values of red light are more sensitive at higher concentrations, and the irradiance values of green light are more sensitive at lower concentrations, permitting expanding the range by using red at the higher concentrations and green at the lower concentrations. The lens focusing and geometry of the two different light sources could also be adjusted so as to make one said light source provide better sensitivity in one range and the other provide better sensitivity in a different range, thereby expanding the overall range. The use of two separate sources and paths through the sample assists in measurement when there are cuvette irregularities or an air bubble at one side.

In addition to calculating platelet concentration, the irradiance values are used to monitor a color index ($I_C = H_{RC}/H_{GC}$) and a scatter index [$I_S = (H_{GA} + H_{RA})/(H_{GC} + H_{RC})$]. These index values are used to identify abnormal collect conditions such as clumping, spillovers, air bubbles, hemolysis, red blood cells, white blood cells, etc. These or other ratios could be used to monitor concentration. An advantage of using ratios is inherent discrimination against error sources.

Other Embodiments

Other embodiments of the invention are within the scope of the following claims.

E.g., other methods of solving Equations 1 and 2 can be used. Other equations besides Equations 3 and 4 can be used as approximations; other solutions could be used, and a look up table could be constructed to described the curves in FIG. 4. The method and apparatus could also be used in other blood separation procedures and to monitor components besides platelets.

What is claimed is:

1. A method of monitoring concentration of components of blood flowing in a flowpath comprising
    flowing said components through a transparent channel,
    directing light to said channel along an axis intersecting said channel,
    detecting light passing through said channel along said axis with a central detector,
    detecting light scattered off of said axis with an annular detector, and
    determining condition of components based on said light passing along said axis and/or said light scattered off said axis,
    said determining involving using said central detector to determine concentration in a low range of concentration values and said annular detector to determine concentration in a high range of concentration values.

2. The method of claim 1 wherein said determining involves using said central detector to determine concentration below a point of inflection of an irradiance versus concentration function of light sensed by the annular detector and using the annular detector to determine concentration above two times said point of inflection.

3. The method of claim 1 wherein said determining also involves determining the ratio of light detected by said central detector and said annular detector to provide an index of scatter.

4. The method of claim 1 wherein said detectors are photodetectors providing signals, the magnitudes of said signals being functions of the detected light, and normalized irradiance values are employed in said determining.

5. The method of claim 4 wherein said directing light involves pulsing a light source on and off, and said normalized irradiance values are based on the difference in the magnitudes of said signals between on and off conditions.

6. The method of claim 5 wherein said detecting involves sampling the signals at a frequency that is a multiple of the ambient light frequency.

7. The method of claim 1 wherein said directing light includes directing light of different frequencies.

8. The method of claim 1 wherein said transparent channel is a plastic cuvette of a disposable tubing set.

9. The method of claim 8 further comprising separating blood from a patient/donor into separated fractions and directing one fraction to said transparent channel.

10. The method of claim 9 wherein said fraction comprises platelets and further comprising collecting said platelets after they have passed through said transparent channel.

11. The method of claim 8 further comprising providing a movable cover, and blocking ambient light from said channel and detectors with said cover during said directing and detecting.

12. Apparatus for monitoring concentration of components of blood flowing in a flowpath comprising
    a transparent channel,
    a source of light positioned to direct light to said channel along an axis intersecting said channel,
    a central light detector positioned to detect said light passing through said channel along said axis and provide a central signal indicating said passing light, an annular detector positioned to detect said light scattering off of said axis and provide an annular signal indicating said scattered light, and a calculator connected to receive said central signal and said annular signal from said central and annular detectors and to determine conditions of components based upon said central signal and/or said annular signal, said calculator using said central signal to determine concentration in a low range of concentration values and said annular signal to determine concentration in a high range of concentration values.

13. The apparatus of claim 12 wherein said calculator uses said central signal to determine concentration below a point of inflection of an irradiance versus concentration function of light sensed by the annular detector and uses the annular detector to determine concentration above two times said point of inflection.

14. The apparatus of claim 12 wherein said calculator determines the ratio of light detected by said central detector and said annular detector to provide an index of scatter.

15. The apparatus of claim 12 wherein said detectors are photodetectors, and normalized irradiance values are employed by said calculator.

16. The apparatus of claim 15 wherein said source of light is pulsed on and off, and said normalized irradiance values are based on the difference in the magnitudes of said signals between on and off conditions.

17. The apparatus of claim 16 wherein said signals of said detectors are sampled at a frequency that is a multiple of the ambient light frequency.

18. The apparatus of claim 12 wherein said source of light provides light of different frequencies.

19. The apparatus of claim 12 wherein said transparent channel is a plastic cuvette of a disposable tubing set.

20. The apparatus of claim 19 further comprising a blood separating centrifuge for separating blood from a patient/donor into separated fractions, and a tube directing one fraction to said transparent channel.

21. The apparatus of claim 20 wherein said fraction comprises platelets, and further comprising a platelet collection bag for collecting said platelets after they have passed through said transparent channel.

22. The apparatus of claim 19 further comprising a movable cover for blocking ambient light from said channel and detectors.

23. Apparatus for monitoring concentration of components of blood flowing in a flowpath comprising a removable transparent channel comprising a rigid plastic cuvette made of optically clear transparent material permanently connected to flexible plastic tubing of a disposable tube set, a channel engager having a recess for removably receiving said channel, a source of light positioned to direct light to said plastic cuvette along an axis intersecting said plastic cuvette when mounted in said recess, a light detector positioned to detect said light passing through said plastic cuvette when mounted in said recess, and a movable cover movable between an open position in which said plastic cuvette can be placed in said recess and a closed position in which ambient light is blocked from said detector via said cover, said cover enclosing said cuvette within it when in said closed position, said cover including means for guiding said cuvette into a predetermined position aligned with said source of light and said detector as said cover is moved to said closed position and means for holding said cuvette in said position.

24. The apparatus of claim 23 wherein said cover is slidably mounted along said axis.

25. The apparatus of claim 24 wherein said means for guiding and said means for holding comprise notches for receiving circuular extension portions of said cuvette to accurately locate said cuvette with respect to said axis, said notches converging along axes parallel to said axes to guide portions of said plastic cuvette into position.

26. The apparatus of claim 25 wherein said plastic cuvette has flat walls normal to said axis.

27. The apparatus of claim 23 wherein said cuvette has a smooth transition form a circular flowpath of said tube to a rectangular flowpath of said cuvette.

* * * * *